US012564402B2

(12) United States Patent　　　　(10) Patent No.:　US 12,564,402 B2
Gavalis et al.　　　　　　　　　　　(45) Date of Patent:　　　Mar. 3, 2026

(54) REVERSE ANASTOMOSIS CLOSURE CLIP

(71) Applicant: BOSTON SCIENTIFIC SCIMED, INC., Maple Grove, MN (US)

(72) Inventors: Robb Morse Gavalis, Westborough, MA (US); Brittany Elizabeth Reed, Brookline, MA (US); Joseph W. King, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 265 days.

(21) Appl. No.: 18/505,815

(22) Filed: Nov. 9, 2023

(65) Prior Publication Data

US 2024/0197320 A1　　Jun. 20, 2024

Related U.S. Application Data

(60) Provisional application No. 63/387,720, filed on Dec. 16, 2022.

(51) Int. Cl.
　　A61B 17/08　　　　(2006.01)
　　A61B 17/00　　　　(2006.01)
(52) U.S. Cl.
　　CPC .. A61B 17/083 (2013.01); *A61B 2017/00818* (2013.01); *A61B 2017/081* (2013.01); *A61B 2017/088* (2013.01)
(58) Field of Classification Search
　　None
　　See application file for complete search history.

(56) References Cited

U.S. PATENT DOCUMENTS

| | | | | | |
|---|---|---|---|---|---|
| 5,478,354 | A | * | 12/1995 | Tovey | A61B 17/0643 |
| | | | | | 606/104 |
| 7,938,840 | B2 | * | 5/2011 | Golden | A61B 17/32053 |
| | | | | | 606/153 |
| 9,295,463 | B2 | * | 3/2016 | Viola | A61B 17/10 |
| 10,835,261 | B2 | * | 11/2020 | Menn | A61B 17/122 |
| 2002/0082614 | A1 | * | 6/2002 | Logan | A61B 17/11 |
| | | | | | 606/139 |
| 2002/0091398 | A1 | * | 7/2002 | Galdonik | A61B 46/17 |
| | | | | | 606/153 |

(Continued)

FOREIGN PATENT DOCUMENTS

WO　　　　2019/226817　　　11/2019

*Primary Examiner* — Shaun L David
(74) *Attorney, Agent, or Firm* — Fay Kaplun & Marcin, LLP

(57)　　　　　　ABSTRACT

A system includes a clip, a member and a control member. The clip includes a barrel member defines a cavity therein and clip arms. Distal ends of the arms are connected to one another and slidably received within the cavity to be moved between open and closed configurations. The member includes a lumen extending longitudinally therethrough. A distal end of the member in contact with the distal ends of the arms to hold the arms distally against the barrel member. The control member is slidably received within the lumen so that a distal end of the control member extends distally past the distal end of the member and the distal ends of the arms to be connected to the distal end of the barrel member. A longitudinal movement of the control member relative to the longitudinal member moves the arms between the open and closed configurations.

15 Claims, 6 Drawing Sheets

(56)                     References Cited

U.S. PATENT DOCUMENTS

| | | | |
|---|---|---|---|
| 2005/0021054 A1* | 1/2005 | Ainsworth | A61B 17/0057 |
| | | | 606/143 |
| 2007/0198058 A1* | 8/2007 | Gelbart | A61B 17/0057 |
| | | | 606/213 |
| 2008/0051703 A1 | 2/2008 | Thornton et al. | |
| 2012/0029532 A1* | 2/2012 | Hodgkinson | A61B 17/0057 |
| | | | 606/139 |
| 2012/0296354 A1* | 11/2012 | Hsu | A61B 17/068 |
| | | | 606/153 |
| 2016/0220261 A1* | 8/2016 | Menn | A61B 17/122 |
| 2017/0079629 A1* | 3/2017 | Malanowski | A61B 17/068 |
| 2017/0079633 A1* | 3/2017 | Dickson | A61B 17/00234 |
| 2017/0079658 A1* | 3/2017 | Walters | A61B 17/0644 |
| 2019/0357933 A1* | 11/2019 | Golden | A61B 17/00234 |
| 2021/0077186 A1* | 3/2021 | Pate | A61B 18/1492 |

* cited by examiner

REVERSE ANASTOMOSIS CLOSURE CLIP

PRIORITY CLAIM

The present disclosure claims priority to U.S. Provisional Patent Application Ser. No. 63/387,720 filed Dec. 16, 2022; the disclosure of which is incorporated herewith by reference.

FIELD

The present disclosure relates to a minimally invasive procedure such as Endoscopic Ultrasound (EUS) procedure. In addition, the present disclosure relates to a reverse anastomosis clipping system.

BACKGROUND

Endoscopic Ultrasound (EUS) is a minimally invasive procedure performed with a specialized endoscope that uses high frequency soundwaves to visualize the digestive (gastrointestinal) tract and other structures. Thus, it is desirable to combine the diagnostic specificity made possible via EUS with therapeutic technology to provide non-invasive treatment of gastrointestinal issues. According to one application, a lumen-apposing metal stent (LAM) such as, for example, the AXIOS™ Stent, may be used to create an anastomotic conduit between two lumens—e.g., a wall of the gastrointestinal tract and a neighboring fluid-filled cavity—for EUS-guided transluminal drainage of pancreatic fluid collections.

While LAMs are commonly used to provide access between adherent structures (e.g., stomach/duodenum and pancreatic pseudocyst) as described above, physicians have been hesitant to use LAMs with non-adherent structures since time is required to create a permanent fistula between the two structures prior to the LAMs removal. In these cases, if the LAM is removed or shifts early, there is a risk of leakage. Leakage would require surgical intervention as there is currently no endoscopic methodology via which an opening or puncture within a far structure (e.g., a structure desired to be connected to a wall of the gastrointestinal tract via the LAM) may be closed.

SUMMARY

The present disclosure relates to a reverse anastomosis clipping system. The system includes a clip having a barrel member extending from an open proximal end to a closed distal end to define a cavity therein and a pair of clip arms. Distal ends of the clip arms are connected to one another and slidably received within the cavity of the barrel member to be moved between an open configuration, in which proximal ends of the clip arms are separated from one another to receive a target tissue therebetween, and a closed configuration, in which the proximal ends of the clip arms are moved toward one another to grip the target tissue. The system also includes a longitudinal member extending between the clip arms from a proximal end to a distal end and including a lumen extending longitudinally therethrough. The distal end of the longitudinal member are in contact with the distal ends of the clip arms to hold the clip arms distally against the barrel member. In addition, the system includes a control member slidably received within the lumen of the longitudinal member so that a distal end of the control member extends distally past the distal end of the longitudinal member and the distal ends of the clip arms to be connected to the distal end of the barrel member. A longitudinal movement of the control member relative to the longitudinal member moves the clip arms between the open and closed configurations.

In an embodiment, the control member is releasably connected to the barrel member.

In an embodiment, the distal end of the control member is connected to a remaining length of the control member via a joint configured to separate the enlarged distal end from the remaining length when subject to a force exceeding a predetermined threshold value.

In an embodiment, the proximal end of each of the clip arms includes a pair of fingers, each of the fingers extending along opposing sides of the longitudinal member when the clip is in the closed configuration so that each of the fingers of a first one of the clip arms extends toward a corresponding finger of a second one of the clip arms.

In an embodiment, the fingers of each of the clip are pointed, and the fingers of the first one of the clip arms overlap the fingers of a second one of the clip arms, when the clip arms are in the closed configuration.

In an embodiment, each of the fingers of the first one of the clip arms is sized and shaped to correspond to a corresponding finger of the second one of the clip arms so that the fingers of the first and second clip arms interlock one another, when the clip arms are in the closed configuration.

In an embodiment, the clip arms are formed via a single-piece element that is bent to define the clip arms, a bend extending along the single-piece element between the distal ends of the clip arms.

In an embodiment, the bend of the single-piece element includes an opening extending therethrough, the opening sized, shaped and configured to receive the control member therein.

In an embodiment, each of the clip arms includes a locking tab extending laterally outward therefrom and configured to engage a corresponding engaging feature of the barrel member in a locked configuration.

In an embodiment, the corresponding engage feature includes a window extending through a wall of the barrel member, the window configured to receive the locking tab therein.

In an embodiment, the clip arms are biased toward the open configuration so that, when the barrel member is moved proximally over the clip arms, the clip arms are constrained toward the closed configuration, and when the barrel member is slid distally along the clip arms, the clip arms are permitted to revert to their biased open configuration.

In addition, the present disclosure relates to a reverse anastomosis clipping system. The system includes a lumen-apposing metal stent configured to provide a temporary pathway between a first structure along a gastrointestinal tract and a second structure further along the gastrointestinal tract than the first structure via a first tissue perforation through a wall of the first structure and a second tissue perforation through a wall of the second structure. The system also includes a clip configured to be inserted into the second structure via the second tissue perforation upon removal of the lumen-apposing metal stent to close the second tissue perforation from an interior of the second structure, the clip including a pair of clip arms. Distal ends of the clip arms are connected to one another and received within a cavity of a barrel member to be moved relative thereto between an open configuration, in which proximal ends of the clip arms are separated from one another, and a closed configuration, in which the proximal ends of the clip arms are moved toward one another. In addition, the system includes a longitudinal member extending from a proximal end to a distal end and including a lumen extending therethrough. The longitudinal member is positioned between the clip arms such that the distal end of the longitudinal member is pressed distally against the distal ends of the clip arm to hold the clip arms distally against the barrel member.

Furthermore, the system includes a control member slidably received within the lumen of the longitudinal member. The control member extends from a proximal end to a distal end that extends distally past the distal end of the longitudinal member and the distal ends of the clip arms to be releasably connected to the distal end of the barrel member. A longitudinal movement of the control member relative to the longitudinal member moves the clip arms between the open and closed configurations.

In an embodiment, the distal end of the control member is an enlarged ball received within a correspondingly shaped socket along a proximal face of a distal end of the barrel member, the enlarged ball connected to a remaining length of the control member via a joint configured to separate the enlarged distal end from the remaining length when subject to a force exceeding a predetermined threshold value.

In an embodiment, the proximal end of each of the clip arms includes a pair of fingers, each of the fingers extending along opposing sides of the longitudinal member when the clip is in the closed configuration so that each of the fingers of a first one of clip arms extends toward a corresponding finger of a second one of the clip arms.

In an embodiment, each of the clip arms including a locking tab extending laterally outward therefrom and configured to engage a corresponding window extending through a wall of the barrel member to lock the barrel member over the clip arms in the closed configuration.

In addition, the present disclosure relates to a method for treating a tissue defect from a far side of the tissue defect. The method includes inserting a clip, in a closed configuration, into a gastrointestinal structure via a tissue perforation through a wall thereof, the clip including a pair of clip arms, distal ends of which are connected to one another and slidably received within a cavity of a barrel member; moving the clip from the closed configuration, in which proximal ends of the clip arms are drawn toward one another, to an open configuration, in which proximal ends of the clip arms are moved away from one another, by moving the barrel member distally along the clip arms to permit the clip arms to revert toward a biased configuration; and positioning the clip arms about the tissue perforation and moving the clip toward the closed configuration so that surrounding the tissue perforation is drawn between the clip arms and gripped therebetween.

In an embodiment, the clip is moved between the open and closed configurations by moving a control member connected to the barrel member longitudinally relative to a longitudinal member within which it is received, the longitudinal member positioned between the clip arms such that the distal end of the longitudinal member is pressed distally against the distal ends of the clip arms to hold the clip arms distally against the barrel member, and the control member slidably received within the longitudinal member, a distal end of the control member extending distally past the distal end of the longitudinal member and the distal ends of the clip arms to be connected to the distal end of the barrel member.

In an embodiment, the tissue surrounding the tissue perforation is gripped between the clip arms and about the longitudinal member via a pair of fingers at the proximal end of each of the clip arms, each of the fingers extending along opposing sides of the longitudinal member when the clip is in the closed configuration so that each of the fingers of a first one of clip arms extends toward a corresponding finger of a second one of the clip arms.

In an embodiment, the method further includes locking the clip in the closed configuration by drawing the barrel member further proximally over the clip arms until locking tabs extending laterally outwardly from the clip arms engage a corresponding engaging window extending through a wall of the barrel member.

In an embodiment, the method further includes deploying the clip by drawing the control member further proximally relative to the longitudinal member until a force exerted on the control member meets a predetermined threshold value required to separate the control member from the barrel member.

BRIEF DESCRIPTION

DETAILED DESCRIPTION

Figure 1:
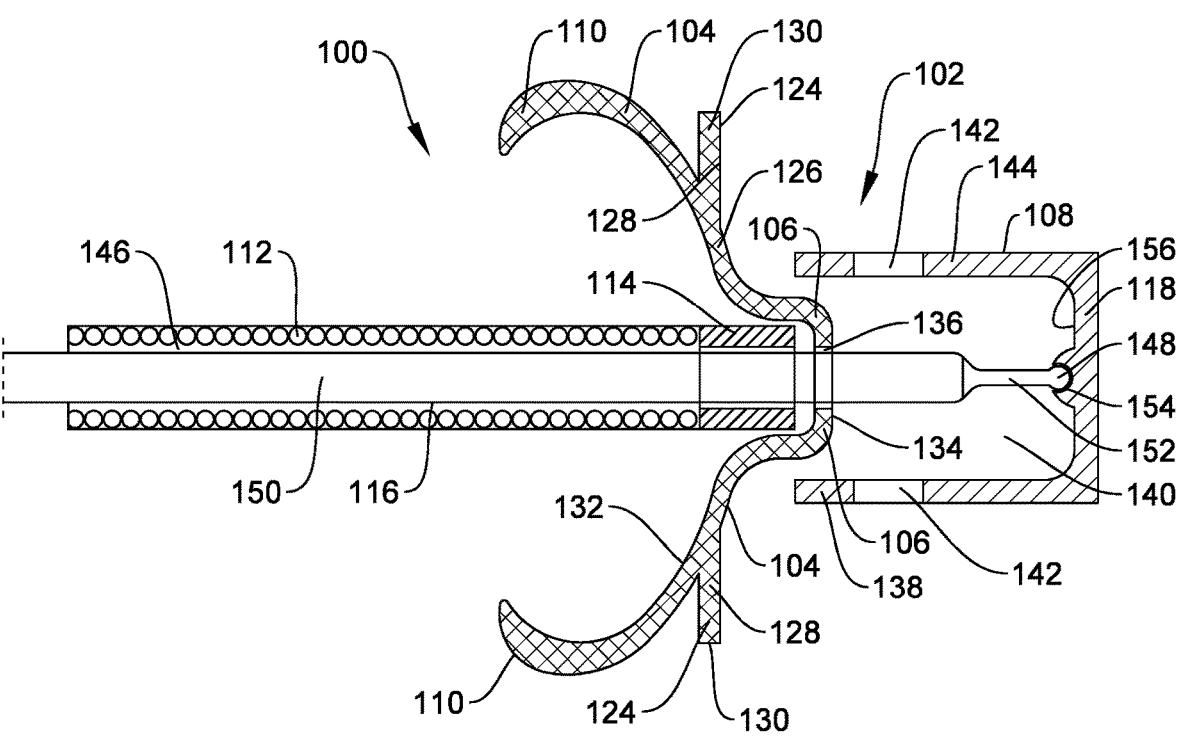
FIG. 1 shows a longitudinal cross-sectional view of a distal portion of a system according to an exemplary embodiment of the present disclosure, in an open configuration.
Figure 2:
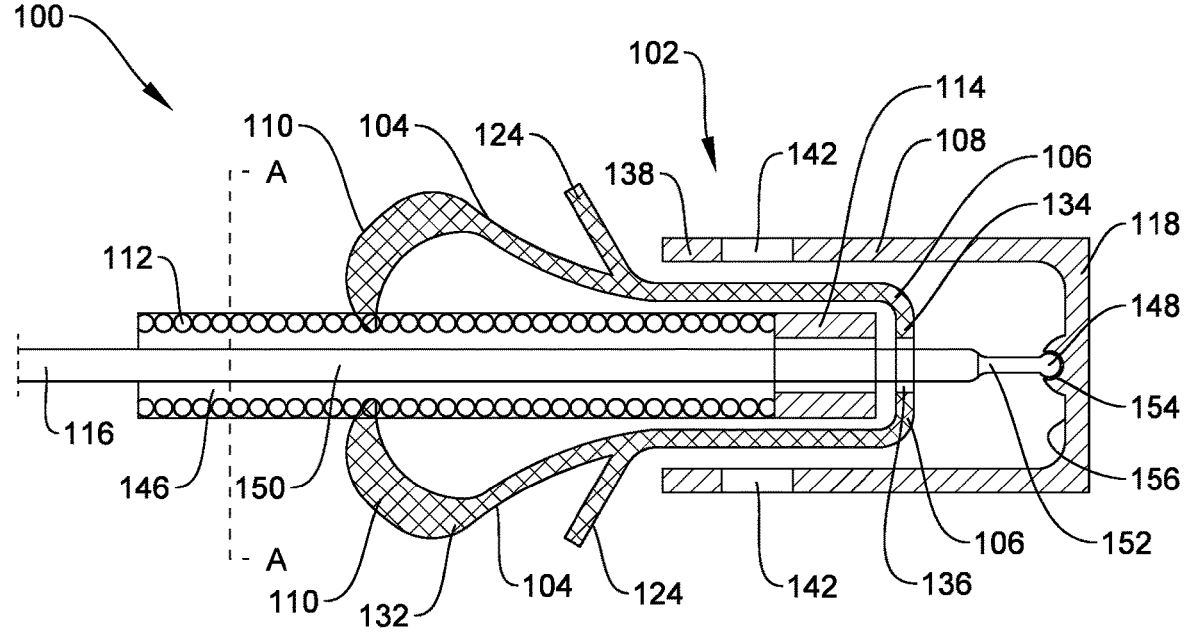
FIG. 2 shows a longitudinal cross-sectional view of the distal portion of the system of FIG. 1, in a closed configuration.

The present disclosure may be further understood with reference to the following description and appended drawings, wherein like elements are referred to with the same reference numerals. The present disclosure relates to an endoscopic treatment system and, in particular, relates to an endoscopic tissue clipping system. Exemplary embodiments of the present disclosure comprise a reverse anastomosis clipping system including a clip that is capable of clipping a target tissue to close a tissue defect such as, for example, a perforation, puncture, or other tissue opening, from a far side of the tissue defect—i.e., from a surface of the tissue facing away from a user (e.g., physician) or operator of the system. In an exemplary embodiment, the reverse anastomosis clipping system may be used in conjunction with a lumen-apposing metal stent (LAM), which may be placed to create a temporary pathway between two nonadherent structures—a first proximal structure (e.g., stomach) and a second distal structure (e.g., jejunum)—so that an endoscope may be passed therethrough, from within the first structure to an interior of the second structure, to provide treatment deeper within the GI tract.

Once treatment has been provided, the LAM is removed, leaving a first perforation in a wall of the first structure and a second perforation in a wall of the second structure where the LAM had been positioned. The exemplary clipping system may be inserted from the first structure into the second structure via the second perforation so that the second perforation may be clipped from within. This allows the clip to remain in the second structure, in the clipped configuration, so that upon healing of the second perforation, the clip will pass naturally through the body.

The first perforation may be closed using a conventional hemostasis clip. Although the exemplary embodiments show and describe the clip as being used in conjunction with a LAM placed to provide a temporary pathway between nonadherent structures, it will be understood by those of skill in the art that the clipping system of the present disclosure may be utilized in any of a variety of situations in which it is desired to clip a tissue defect from a far (e.g., distal) side of the defect including, for example, a recovery of procedures (e.g., pancreatic fluid collections) in which complications (e.g., migrating LAM, perforations, bleeds) arise during the procedure. It will also be understood by those of skill in the art that the terms "proximal" and "distal," as used herein, are intended to refer to a direction toward (proximal) and away from (distal) a user of the device (e.g., physician).

As shown in FIGS. 1-6, a reverse anastomosis clipping system 100 comprises a clip 102 configured to be inserted into a patient body to clip target tissue from a far side of the target tissue—e.g., along a tissue surface facing away from a user of the system 100. The clip 102 includes a pair of clip arms 104, distal ends 106 of which are connected to one another and slidably received within a barrel member 108 so that the clip arms 104 are movable between an open configuration (shown in FIG. 1), in which proximal ends 110 thereof are separated from one another to receive target tissue therebetween, and a closed configuration (shown in FIG. 2), in which the proximal ends 110 are drawn toward one another to clip tissue received therebetween.

The system 100 further comprises a longitudinal member 112 positioned between the clip arms 104 so that a distal end 114 of the longitudinal member 112 is in contact with the distal ends 106 of the clip arms 104 to hold the clip arm 104 distally against the barrel member 108. The member 112 of this embodiment is a non-compressible, flexible tube (e.g., similar to a Bowden cable) with a cap/termination at the distal end 114. A control member 116 extends through the longitudinal member 112 and the distal ends 106 of the clip arms 104 to be releasably coupled to a distal end 118 of the barrel member 108. Thus, moving the control member 116 longitudinally relative to the longitudinal member 112 correspondingly moves the barrel member 108 relative to the clip arms 104 to move the clip 102 between the open configuration and the closed configuration. In particular, drawing the control member 116 proximally relative to the longitudinal member 112 draws the barrel member 108 proximally over the clip arms 104 to move the clip 102 toward the closed configuration, while advancing the control member 116 distally relative to the longitudinal member 112 allows the clip arms 104 to be moved proximally out of the barrel member 108 toward the open configuration.

Figure 3:
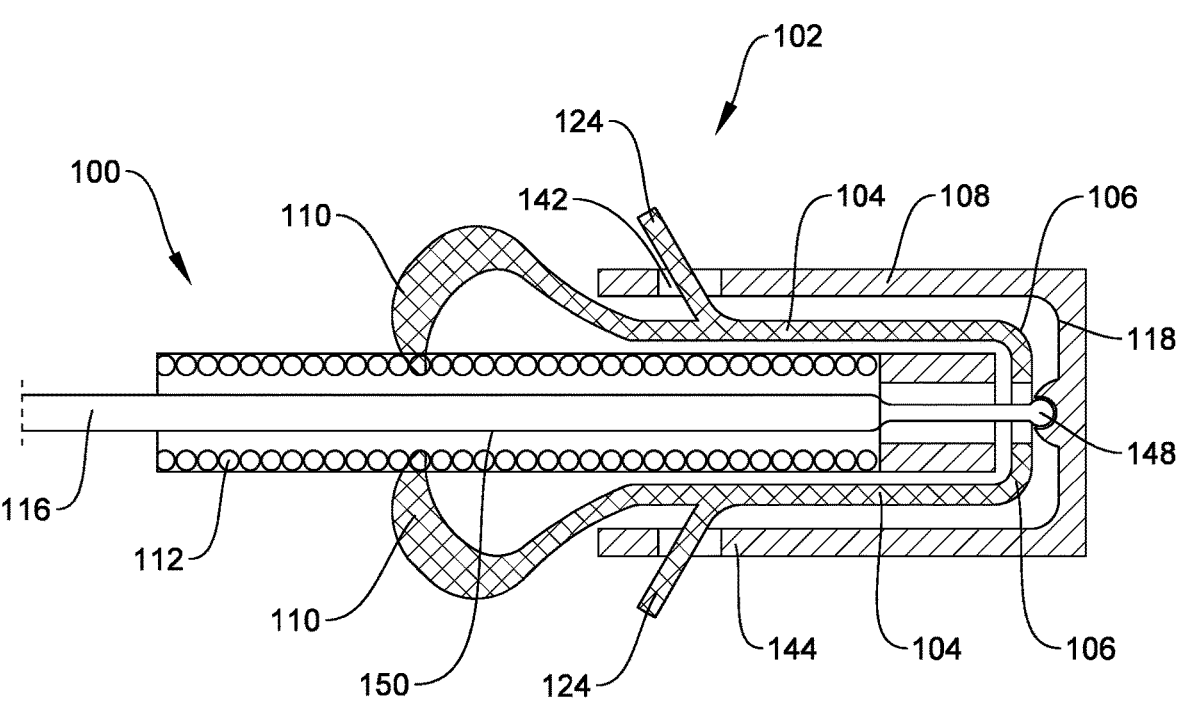
FIG. 3 shows a longitudinal cross-sectional view of the distal portion of the system of FIG. 1, in a locked configuration.
Figure 4:
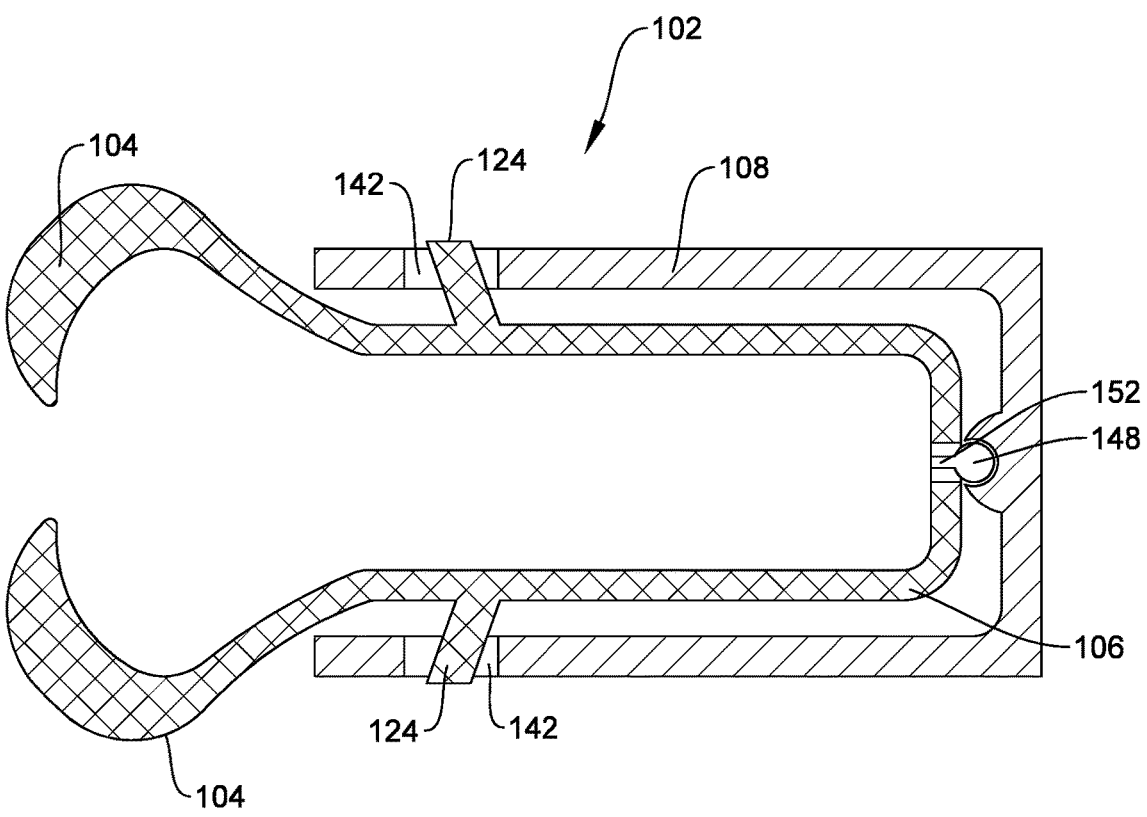
FIG. 4 shows a longitudinal cross-sectional view of the distal portion of the system of FIG. 1, in a deployed configuration.

Upon clipping of the target tissue as desired, the control member 116 may be drawn further proximally relative to the longitudinal member 112 to lock the barrel member 108 over the clip arms 104 in the closed configuration, as shown in FIG. 3. Once the clip 102 is locked in the closed configuration, the control member 116 may be moved even further proximally until the control member 116 is separated or otherwise released from the barrel member 108 to deploy the clip 102 in the body, as shown in FIG. 4, as will be described in further detail below.

Figure 5:
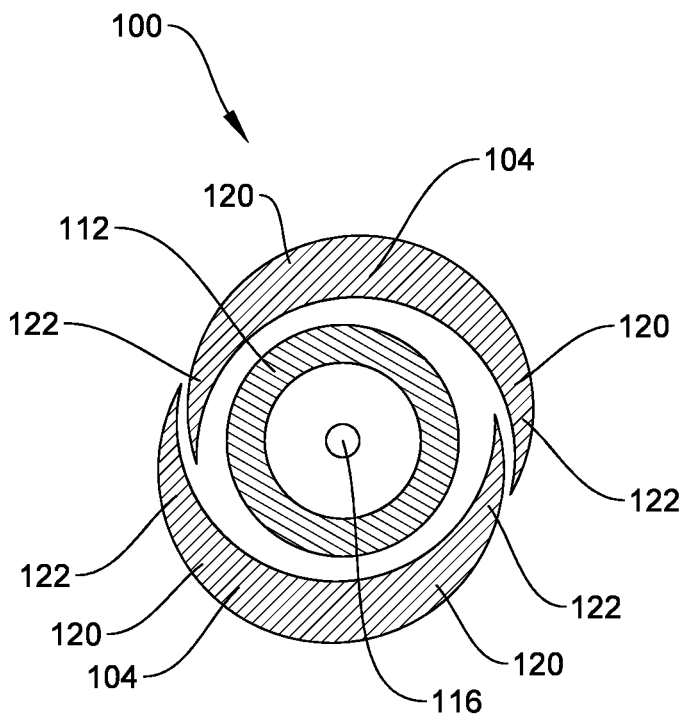
FIG. 5 shows a cross-sectional view of the distal portion of the system according to FIG. 1, along a line A-A of FIG. 2.

As described above, the clip arms 104 extend from distal ends 106 which are connected to one another, to proximal ends 110 which are movable toward and away from one another between the closed configuration and the open configuration, respectively. The proximal end 110 of each of the clip arms 104 includes a pair of inwardly curved fingers 120 which are sized, shaped and configured so that, when the clip arms 104 are moved toward the closed configuration, the fingers 120 of each of the clip arms 104 extend around and along opposing sides of the longitudinal member 112, as shown in FIG. 5. Thus, when the clip 102 is moved to the closed configuration, each of the fingers 120 of a first one of the clip arms 104 extends toward a corresponding finger 120 of a second one of the clip arms 104 to grip target tissue therebetween. In an exemplary embodiment, a proximal end 122 of each of the fingers 120 includes a gripping feature for facilitating gripping of tissue between the clip arms 104.

Figure 6:
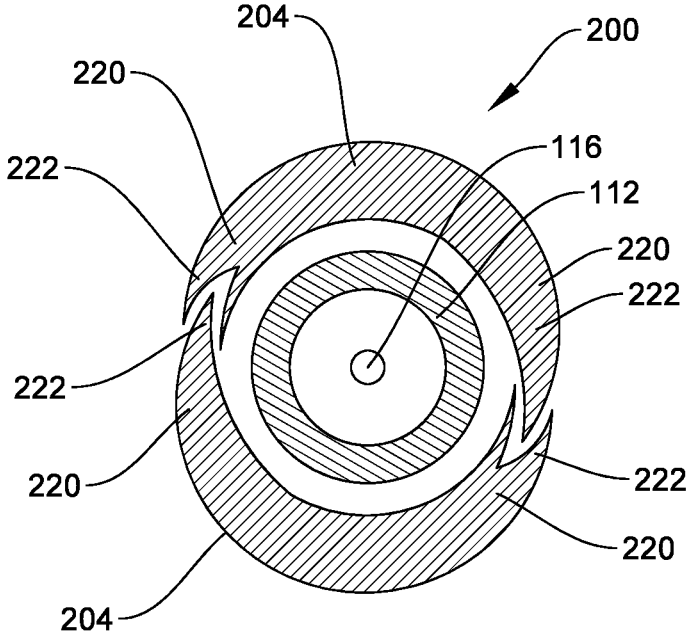
FIG. 6 shows a cross-sectional view of a distal portion of a system according to an alternate embodiment of the system of FIG. 1 along line A-A.

In one example, as shown in FIG. 5, proximal ends 122 of the fingers 120 taper toward a pointed tip so that when the clip arms 104 are moved toward the closed configuration, the pointed tips of corresponding ones of the fingers 120 overlap one another to grip tissue therebetween. In another example, as shown in FIG. 6, a proximal end 222 of each finger 220 of a first one of clip arms 204 is sized and shaped to correspond to the proximal end 222 of a corresponding finger 220 of a second one of the clip arms 204 so that, when the clip arms 204 are drawn toward one another, the fingers 220 of the first one of the clip arms 204 interlock with the fingers 220 of the second one of the clip arms 204. It will be understood by those of skill in the art, however, that proximal ends 122, 222 of fingers 120, 220 of clip arms 104, 204 may have any of a variety of configurations so long as the fingers 120, 220 thereof are configured to grip tissue therebetween. Also, as would be understood by those skilled in the art, the tissue gripping features may be located around/on the side of the member 112 where the fingers 220 of the clip arms come together. While this may impart some increased tissue pressure to the shaft, because the locking mechanism is to the side with jaw to jaw contact the shaft will be able to be withdrawn and not disrupt the tissue opposition between the jaws.

In an exemplary embodiment, the clip arms 104 are biased toward the open configuration so that, when the barrel member 108 is moved distally relative to the clip arms 104, the clip arms 104 are gradually unconstrained as they move proximally out of the barrel member 108 so that the proximal ends 110 of the clip arms 104 move apart from one another, into the open configuration, under their natural bias. When the barrel member 108 is drawn proximally over the clip arms 104, the clip arms 104 are constrained via a wall of the barrel member 108, toward the closed configuration so that fingers 120 of each of the clip arms 104 are drawn radially inward to extend around the longitudinal member 112 along opposing sides of the longitudinal member 112.

Each of the clip arms 104 may also include a locking feature configured to engage a portion of the barrel member 108 to lock the barrel member 108 over the clip arms 104 in the closed configuration. In an exemplary embodiment, the feature includes a locking tab 124 extending laterally outward therefrom (e.g., one locking tab on each of the clip arms 104). Each locking tab 124 extends from an exterior surface 126 of a corresponding one of the clip arms 104, facing away from the longitudinal member 112.

As will be described in further detail below, the locking tab 124 is sized, shaped and configured to engage a portion of the barrel member 108 so that, when the locking tab 124 engages the barrel member 108, the clip arms 104 are locked relative to the barrel member 108, in the closed configuration. In an exemplary embodiment, each locking tab 124 is biased toward a locking configuration in which the locking tab 124 extends laterally outward from a longitudinal axis of the clip 102. A distal end 128 of each of the locking tabs 124 is connected to the exterior surface 126 of the clip arm 104 and each of the locking tabs 124 extends to a proximal end 130 free to move relative to the proximal end 110 of the clip arm 104.

Each locking tab 124 is configured to be deflected toward the longitudinal axis of the clip 102 (i.e., the proximal end of each of the locking tabs 124 is pushed radially inward toward the longitudinal axis by contact with the barrel member 108) and the exterior surface 126 of the clip arm 104 as the barrel member 108 is slid proximally thereover. The proximal end 130 of each of the locking tabs 124 then springs laterally away from the longitudinal axis of the clip 102 under its natural bias into a locking configuration as it reaches the corresponding engaging window 142. The angle of the laterally extending locking tab 124 is selected such that, once one or both of the locking tabs 124 are received within the corresponding engaging windows 142 in the locked configuration, the barrel member 108 is prevented from being moved distally off of the clip arms 104.

According to one exemplary embodiment, the clip arms 104 are formed from a single element 132 including a bend 134 to define the pair of the clip arms 104. The bend 134 in this embodiment extends between the distal ends 106 of the clip arms 104 and includes an opening 136 extending therethrough. The opening 136 is sized and configured to receive the control member 116 therethrough. It will be understood by those of skill in the art, however, that the clip arms 104 may be formed from more than one element and may have any of a variety of configurations so long as the distal ends 106 are connected to one another and able to accommodate the control member 116 so that the clip arms 104 may be moved between the open and closed configurations, as described herein.

The barrel member 108 extends from a closed distal end 118 to an open proximal end 138 so that a cavity 140 is defined therein. The distal ends 106 of the clip arms 104 are slidably received within the cavity 140 and configured to be moved longitudinally relative thereto so that the clip arms 104 are movable between the open and the closed configurations. The barrel member 108 includes engaging features configured to engage the locking features of the clip arms 104. In an exemplary embodiment, a length of the barrel member 108 is selected so that, when the barrel member 108 is locked over the clip arms 104, the distal end 118 of the barrel member 108 is in contact with and/or engages the distal ends 106 (or bend 134) of the clip arms 104 to prevent further proximal movement of the barrel member 108 relative to the clip arms 104.

As described above, in an exemplary embodiment, the engaging features include engaging windows 142 extending through a wall 144 of the barrel member 108, with each of the engaging windows 142 being sized, shaped and configured to receive a corresponding one of the locking tabs 124 therein. The engaging windows 142 extend through a portion of the wall 144 positioned so that, when the locking tabs 124 are received within the engaging windows 142, the clip 102 is locked in the closed configuration. To lock the barrel member 108 over the clip arms 104, the barrel member 108 is drawn proximally relative to the clip arms 104 until each of the locking tabs 124 springs outward through a corresponding one of the engaging windows 142.

Although the exemplary embodiment shows and described the clip arms 104 as including locking tabs 124 and the barrel member 108 including engaging windows 142, it will be understood by those of skill in the art that the clip arms 104 and the barrel member 108 may include any of a variety of corresponding features or structures configured to engage one another to lock the barrel member 108 over the clip arms 104 in the closed configuration.

The longitudinal member 112 extends from a proximal end (not shown) which, for example, includes an actuator that remains outside the body accessible to the user while the distal end 114 is inserted into the body to a site adjacent to the target tissue to be clipped. The longitudinal member 112 includes a lumen 146 extending therethrough. As described above, the longitudinal member 112 is positioned between the clip arms 104 so that the distal end 114 is in contact with the distal ends 106 of the clip arms 104 to hold the clip arms 104 distally against the barrel member 108. In an embodiment, the distal end 114 of the longitudinal member 112 is pressed or held distally against the bend 134, which extends between the distal ends 106 of the clip arms 104. The longitudinal member 112 may, in one embodiment, include a Bowden cable shaft. It will be understood by those of skill in the art, however, that the longitudinal member 112 may include any catheter or other non-compressible longitudinal element configured to facilitate insertion of the clip 102 through, for example, an endoscope to a target area within a patient body.

The control member 116 is releasably coupled to the barrel member 108, extending from the proximal end (not shown) accessible to the user to a distal end 148. In an exemplary embodiment, the control member 116 extends through the lumen 146 of the longitudinal member 112 and through the opening 136 extending through the bend 134 of the clip arms 104 so that the distal end 148 extends distally past the distal ends 106 of the clip arms 104 to be connected to the distal end 118 of the barrel member 108. Thus, the control member 116 may be moved longitudinally relative to the longitudinal member 112, which holds the clip arms 104 distally against the barrel member 108, to move the barrel member 108 longitudinally relative to the clip arms 104 so that the clip 102 may move between the open and the closed configurations.

In particular, moving the control member 116 proximally relative to the longitudinal member 112 draws the barrel member 108 proximally over the clip arms 104 so that the proximal ends 110 of the clip arms 104 are moved radially inward toward one another and toward the longitudinal member 112 extending therebetween. Thus, when the proximal ends 110 of the clip arms 104 are positioned proximate tissue and moved toward the closed configuration, tissue is gripped between the fingers 120 of the clip arms 104 and pressed against the longitudinal member 112 albeit with less force than the gripping force applied to the tissue by the fingers 120 against the member 112. Moving the control member 116 distally relative to the longitudinal member 112 allows the clip arms 104 to be moved proximally out of the barrel member 108 so that the clip arms 104 may revert toward the open configuration. The clip 102 may be moved between the open and closed configurations, as described, until the target tissue has been gripped as desired.

It will be understood by those of skill in the art that since the clip arms 104 are biased toward the open configuration, moving the control member 116 distally relative to the longitudinal member 112 releases tension therealong so that the barrel member 108 is permitted to slide distally off of the clip arms 104 as the clip arms 104 are moved toward the open configuration under their natural bias. Thus, the clip arms 104 maintain contact with the distal end 114 of the longitudinal member 112 so that the clip arms 104 are held/pressed against the barrel member 108 until final deployment of the clip 102, as will be described in further detail below.

In an exemplary embodiment, the distal end 148 of the control member 116 includes a ball or other enlarged shape configured to be received within a correspondingly shaped socket 154 or recess along a proximal face 156 of the distal end 118 of the barrel member 108. The distal end 148 may be connected to a remaining length 150 of the control member 116 via a joint 152 that is configured to break, release or otherwise separate when subject to a predetermined threshold force. In one embodiment, the joint 152 is configured as a reduced diameter portion of the control member 116. In another embodiment, the joint 152 is configured as an adhesive subject to fail when subject to a force of at least a predetermined magnitude. In yet another embodiment, the joint 152 is configured as a releasable coupling. It will be understood by those of skill in the art, however, that the joint 152 may have any of a variety of configurations so long as the joint 152 is configured to separate the distal end 148 from the remaining length 150 when subject to the predetermined threshold force. In another exemplary embodiment, rather than having a releasable joint 152, the distal end 148 may be coupled to the distal end 118 of the barrel members via a releasable connection subject to break, release or otherwise separate when subject to the predetermined threshold force.

Thus, once the barrel member 108 has been locked over the clip arms 104 and it is desired to move the clip 102 toward the deployed configuration, the control member 116 may be drawn proximally relative to the longitudinal member 112 until the predetermined threshold force is exerted on the control member 116 and the control member 116 is separated from the barrel member 108. The system 100 is configured so that, when this separation occurs, the locking tabs 124 are received within the engaging windows 142 and the clip 102 is locked closed over the clipped tissue when the clip 102 is separated from the longitudinal member 112. The longitudinal member 112 and the control member 116 may then be proximally removed from between the clip arms 104, leaving just the clip 102 clipped over the target tissue.

In a further exemplary embodiment, the clip arms 104 include surface features along the exterior surfaces 126 thereof and/or along the barrel member 108 configured to facilitate echogenic imaging of the clip 102. As would be understood by those skilled in the art, the surface features create angled surfaces so that the variation in the angle of incidence of ultrasound energy varies across the exterior surface 126, resulting in different angles of reflection, including back towards a transducer, to improve visualization through ultrasound imaging.

Figure 7:
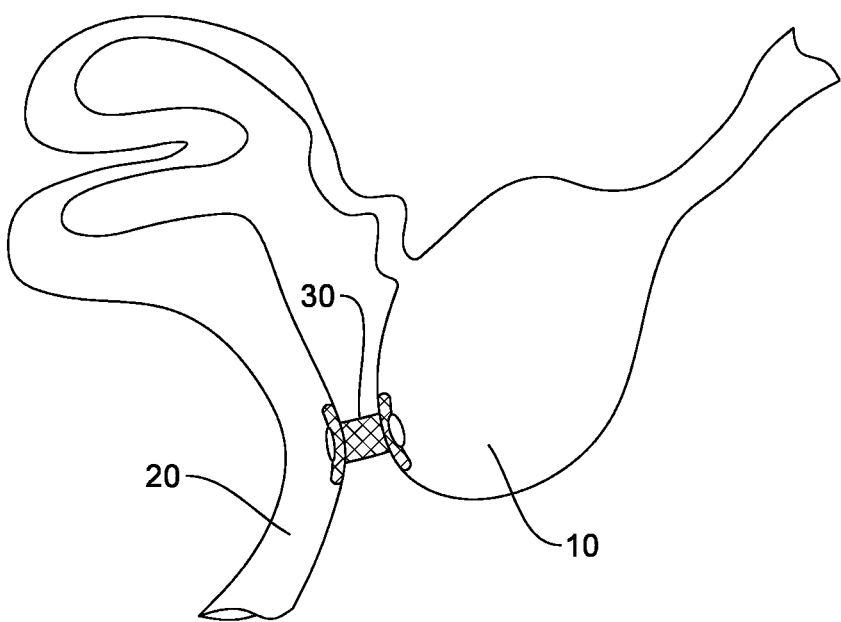
FIG. 7 shows a schematic view of a lumen-apposing metal stent (LAM) to be used as a temporary pathway between neighboring structures along a gastrointestinal tract.
Figure 8:
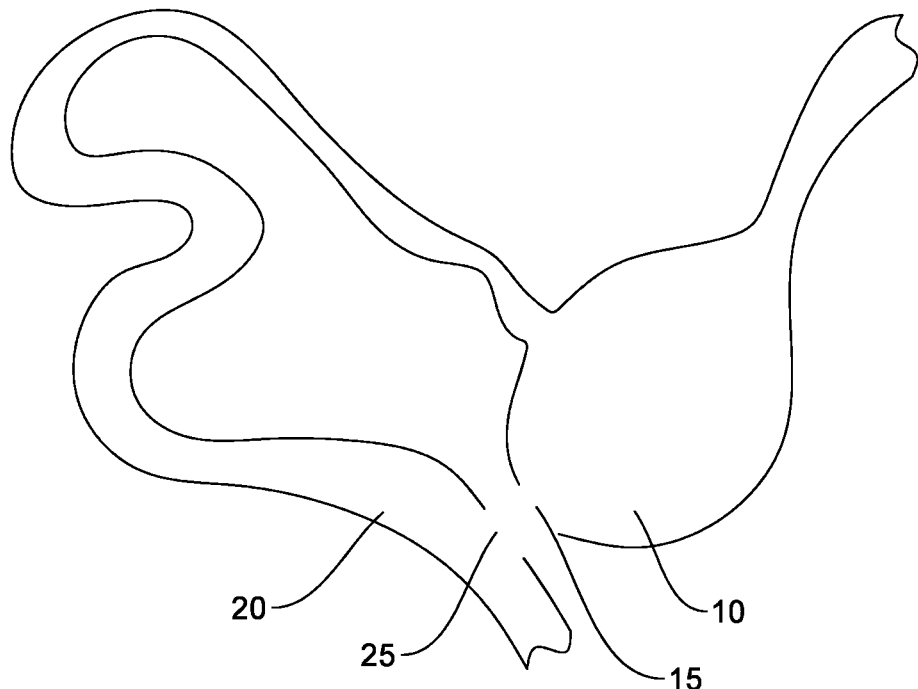
FIG. 8 shows a schematic view of the gastrointestinal tract upon removal of the LAM.

According to an exemplary method utilizing the clipping system 100, the clip 102 is used to treat tissue defects such as, for example, perforations, punctures or other openings of the tissue formed during the creation of a pathway or conduit between neighboring structures. In an exemplary embodiment, a lumen-apposing metal stent (LAM) 30 is used to create a temporary pathway between nonadherent structures of a gastrointestinal (GI) tract of a patient, as shown in FIG. 7. As would be understood by those skilled in the art, the LAM 30 may be used to create a pathway from within a first structure/lumen 10 (e.g., stomach) to an interior of a second structure 20 (e.g., jejunum) further along the GI tract to facilitate the provision of endoscopic treatment(s) to deeper areas along the gastrointestinal (GI) tract. Upon treatment of the GI tract and removal of the LAM 30, as shown in FIG. 8, first and second perforations 15, 25 in the first and second structures 10, 20, respectively, remain and must be closed.

To close such openings, a clip 102 of the system 100 may be inserted into the patient's body in the closed configuration via, for example, an endoscope advanced through natural body lumens (e.g., the esophagus, stomach, etc.). The clip 102 is inserted through the first structure 10 and into the second structure 20 via the first and second perforations 15, 25, respectively. Once the clip 102 has been inserted into the second structure 20, the clip 102 may be moved toward the open configuration by releasing tension along the control member 116 and allowing the barrel member 108 to slide distally along the clip arms 104 as the proximal ends 110 of the clip arms 104 move away from one another under their natural bias.

The proximal ends 110 of the clip arms 104 are then positioned proximate the second perforation 25 and moved toward the closed configuration by drawing the control member 116 proximally relative to the longitudinal member 112 so that the barrel member 108 moves proximally over the clip arms 104. As the clip arms 104 are drawn toward one another toward the closed configuration, tissue is gripped between the fingers 120 of the clip arms 104, to be compressed around and about the longitudinal member 112. The clip 102 may be re-opened if the user does not feel the tissue has been gripped as desired. The clip 102 may be moved between the open and the closed configurations until tissue of the second perforation 25 has been clipped, as desired.

Figure 9:
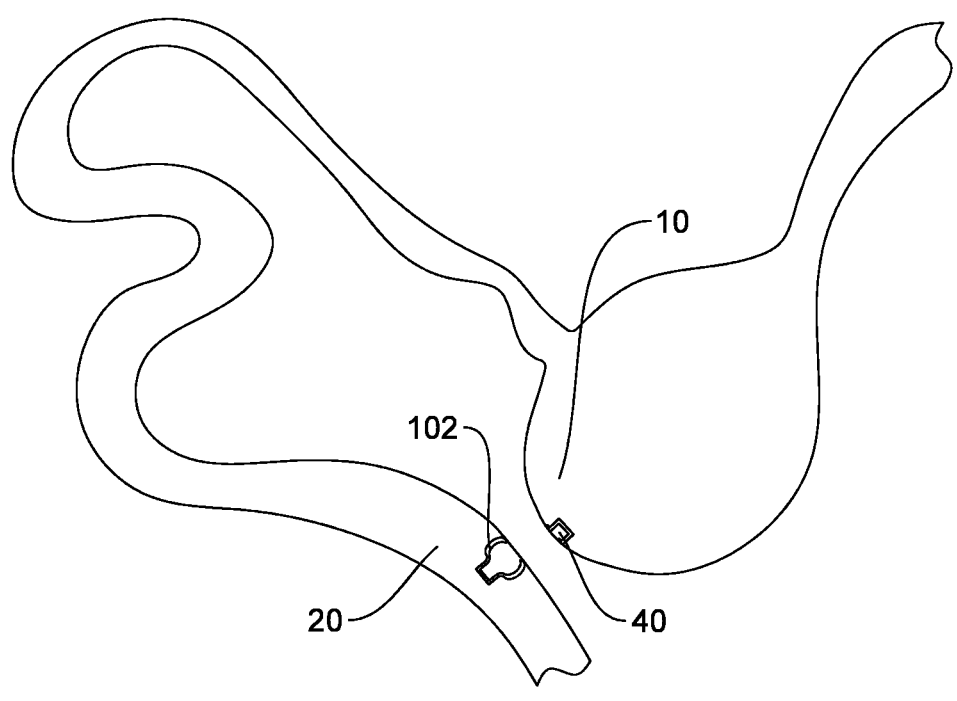
FIG. 9 shows a schematic view of a perforation of a structure of the gastrointestinal tract treated using a clipping system according to an exemplary embodiment of the present disclosure.

Once the tissue of the second perforation 25 has been clipped as desired, the clip 102 is locked in the closed configuration by drawing the control member 116 further proximally relative to the longitudinal member 112 until locking tabs 124 of the clip arms 104 engage the engaging windows 142 of the barrel member 108. Upon locking of the clip 102, the clip 102 may be deployed by drawing the control member 116 even further proximally relative to the longitudinal member 112 until a force exerted on the control member 116 meets a predetermined threshold value, causing the control member 116 to be separated from the barrel member 108. The control member 116 and the longitudinal member 112 are then withdrawn proximally from between the clip arms 104, leaving the clip 102 clipped over the target tissue of the second perforation 25, as shown in FIG. 9.

As will be understood by those of skill in the art, the system 100 enables in-lumen clipping of target tissue of the second structure so that, as the tissue heals, the clip 102 may slough off, passing naturally through the body. Upon clipping of the second perforation 25 of the second structure 20, the first perforation 15 may be treated using one or more conventional hemostasis clips 40 or any other desired method.

Figure 10:
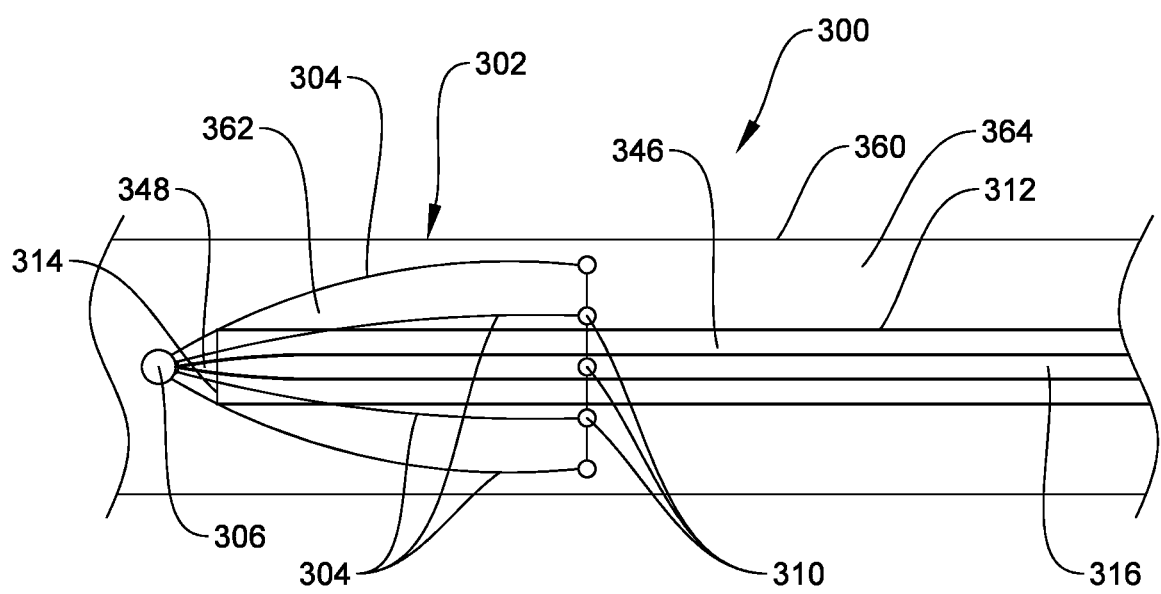
FIG. 10 shows a transparent longitudinal side view of a system according to another exemplary embodiment of the present disclosure.
Figure 11:
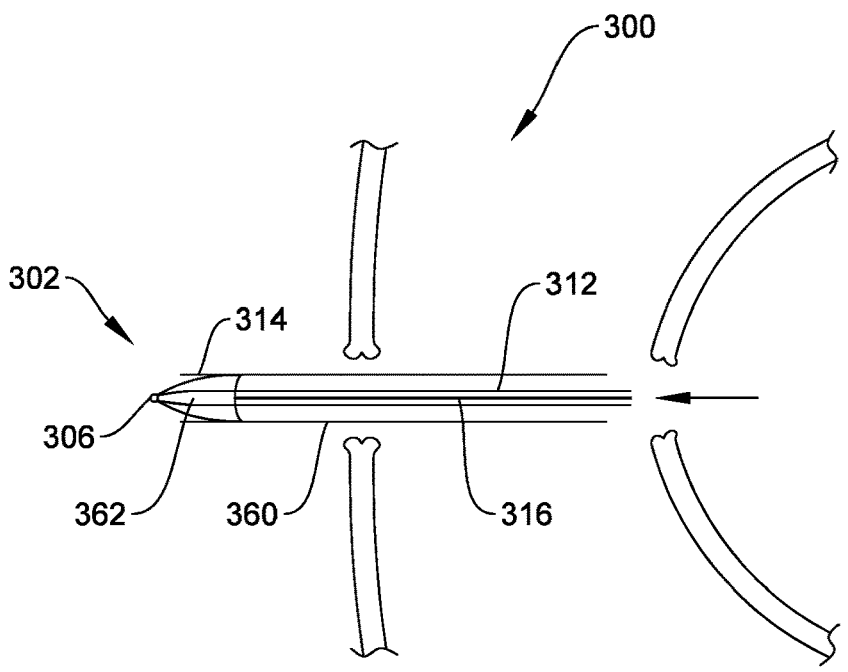
FIG. 11 shows a schematic view of the closure system of FIG. 10, inserted into a target area within a body.
Figure 12:
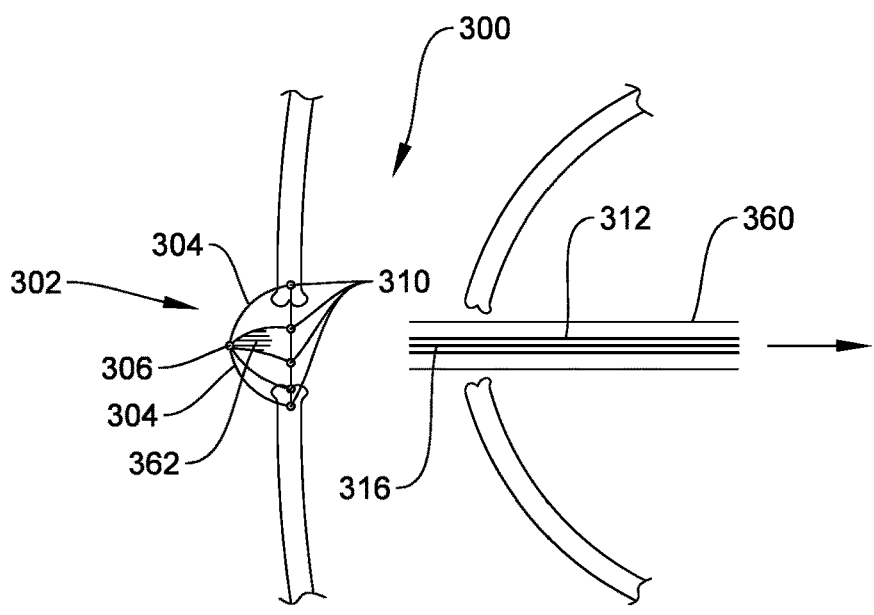
FIG. 12 shows a schematic view of a closure device of the closure system of FIG. 11, deployed in the body.

As shown in FIGS. 10-12, a reverse anastomosis closure system 300 according to another exemplary embodiment of the present disclosure is substantially similar to the system 100 described above except as described below. The system 300 comprises a closure device 302 configured to close a tissue defect from a far side thereof. The system 300 further comprises a longitudinal member 312 configured to facilitate insertion of the closure device 302 to a target area, a control member 316 to facilitate deployment of the closure device 302, and an outer sheath 360 through which the closure device 302 may be delivered to the target area. Similarly to the system 100, the system 300 may be utilized in conjunction with, for example, a LAM that is used to create a temporary pathway between a first structure (e.g., stomach) and a second structure (e.g., jejunum) further along a gastrointestinal (GI) tract of a patient. Upon treatment of the GI tract, the LAM may be removed, leaving a first perforation in the first structure and a second perforation in the second structure. The second structure may be treated in-lumen via the system 300.

As shown in FIG. 10, the closure device 302 includes a plurality of wire struts 304 connected to an expandable, non-permeable membrane 362 so that movement of the struts 304 relative to one another moves the membrane 362 between a folded configuration and an expanded configuration, substantially similarly to an umbrella. The membrane 362 of this embodiment is formed of a non-permeable, biocompatible material such as, for example, a nylon, a rubberized material, or any other suitable material such as polyethylenes, polypropylenes and Teflon, etc. Each of the struts 304 extends from a proximal end 310 to a distal end 306. The distal ends 306 of the struts 304 are movably connected to one another so that, in the folded configuration, the proximal ends 310 are moved toward one another and the membrane 362 is folded onto itself. In the expanded configuration, the proximal ends 310 of the struts 304 are moved radially outward relative to one another to give the membrane 362 a substantially dome shape.

The proximal ends 310 of the struts 304 are tapered and/or pointed so that, when the closure device 302, in the expanded configuration, is drawn proximally against an interior surface of the second structure, the proximal ends 310 grip and/or abut against tissue surrounding the second perforation to facilitate closure of the second perforation. The ends also create an inward force bringing the anastomosis edges closer to one another to promote healing as would be understood by those skilled in the art. In an exemplary embodiment, the proximal ends 310 grip the surrounding tissue of the second perforation so that the membrane 362, in the expanded configuration, completely covers the second perforation, thereby closing it.

The outer sheath 360 is configured as a substantially tubular member sized and shaped to be inserted through, for example, a working channel of an endoscope to a target area (e.g., to an interior of the second structure via the first and second perforations). The outer sheath 360 includes a channel 364 extending therethrough and the channel 364 is sized and shaped to slidably house the closure device 302 therein. In an exemplary embodiment, the struts 304 are biased toward the expanded configuration in which the proximal ends 310 of the struts 304 are separated from one another to give the membrane 362 its expanded, dome shape. When the closure device 302 is received within the outer sheath 360 the closure device 302 is constrained toward the folded configuration. When the closure device 302 is inserted to the target area, however, the closure device 302 may be moved distally out of the outer sheath 360 so that the closure device 302 is permitted to revert to its naturally biased, expanded configuration.

The longitudinal member 312 is substantially similar to the longitudinal member 112, extending longitudinally from a proximal end (not shown) to a distal end 314 and including a channel 346 extending therethrough. The longitudinal member 312 is positioned between the struts 304, the distal end 314 positioned proximally of the connected distal ends 306 of the struts 304, in contact therewith. The longitudinal member 312 may be moved distally relative to the outer sheath 360 to move the closure device 302 from the folded configuration to the expanded configuration. In the folded configuration, the closure device 302 is housed within the outer sheath 360. Moving the longitudinal member 312 distally relative to the outer sheath 360, however, pushes the closure device 302 distally out of the outer sheath 360 so that the closure device 302 is permitted to revert to its biased expanded configuration.

The control member 316 is substantially similar to the control member 116 extending through the channel 346 of the longitudinal member 312 so that a distal end 348 of the control member 316 extends distally from the distal end 314 of the longitudinal member 312 to be connected to the distal ends 306 of the struts 304. Similarly to the control member 116, the control member 316 is configured to be released or otherwise separated from the closure device 302 when subject to a predetermined threshold force. In particular, when it is desired to deploy the closure device 302, the control member 316 is drawn proximally relative to the longitudinal member 312 so that the closure device 302 is pulled proximally against the distal end 314 of the longitudinal member 312 and subjecting the control member 316 to a proximal force.

As described above, the system 300 may be used in a manner substantially similar to the system 100. In an exemplary embodiment, upon insertion of the closure device 302 into the second structure via the second perforation, as shown in FIG. 11, the closure device 302 is moved from the folded configuration toward the expanded configuration by pushing the closure device distally out of the outer sheath 360 via the longitudinal member 312. Once the closure device 302 is in the expanded configuration, the closure device 302 is moved via the control member 316 proximally against tissue surrounding the second perforation, so that the proximal ends 310 of the struts 304 grip the tissue and the membrane 362 completely covers an opening of the second perforation.

The closure device 302 may then be deployed, by drawing the control member 316 further proximally relative to the longitudinal member 312, until the force exerted on the control member 316 reaches the threshold value at which the control member 316 is separated from the closure device 302. The longitudinal member 312 and the control member 316 are then removed from the body, leaving the closure device 302 in-lumen, covering the second perforation as shown in FIG. 12. As discussed above with respect to system 100, the first perforation may then be clipped and/or closed using, for example, a conventional hemostasis clip or any other desired method.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A reverse anastomosis clipping system, comprising:
a clip including a barrel member extending from an open proximal end to a closed distal end to define a cavity therein, and a pair of clip arms, distal ends of which are connected to one another and slidably received within the cavity of the barrel member to be moved between an open configuration, in which proximal ends of the clip arms are separated from one another to receive a target tissue therebetween, and a closed configuration, in which the proximal ends of the clip arms are moved toward one another to grip the target tissue;
a longitudinal member extending between the clip arms from a proximal end to a distal end and including a lumen extending longitudinally therethrough, the distal end of the longitudinal member in contact with the distal ends of the clip arms to hold the clip arms distally against the barrel member; and
a control member slidably received within the lumen of the longitudinal member so that a distal end of the control member extends distally past the distal end of the longitudinal member and the distal ends of the clip arms to be connected to the distal end of the barrel member, a longitudinal movement of the control member relative to the longitudinal member moving the clip arms between the open and closed configurations.

2. The system of claim 1, wherein the control member is releasably connected to the barrel member.

3. The system of claim 2, wherein the distal end of the control member is connected to a remaining length of the control member via a joint configured to separate the enlarged distal end from the remaining length when subject to a force exceeding a predetermined threshold value.

4. The system of claim 1, wherein the proximal end of each of the clip arms includes a pair of fingers, each of the fingers extending along opposing sides of the longitudinal member when the clip is in the closed configuration so that each of the fingers of a first one of the clip arms extends toward a corresponding finger of a second one of the clip arms.

5. The system of claim 4, wherein the fingers of each of the clip are pointed, and the fingers of the first one of the clip arms overlap the fingers of a second one of the clip arms, when the clip arms are in the closed configuration.

6. The system of claim 4, wherein each of the fingers of the first one of the clip arms is sized and shaped to correspond to a corresponding finger of the second one of the clip arms so that the fingers of the first and second clip arms interlock one another, when the clip arms are in the closed configuration.

7. The system of claim 4, wherein the clip arms are formed via a single-piece element that is bent to define the clip arms, a bend extending along the single-piece element between the distal ends of the clip arms.

8. The system of claim 7, wherein the bend of the single-piece element includes an opening extending therethrough, the opening sized, shaped and configured to receive the control member therein.

9. The system of claim 1, wherein each of the clip arms includes a locking tab extending laterally outward therefrom and configured to engage a corresponding engaging feature of the barrel member in a locked configuration.

10. The system of claim 9, wherein the corresponding engage feature includes a window extending through a wall of the barrel member, the window configured to receive the locking tab therein.

11. The system of claim 1, wherein the clip arms are biased toward the open configuration so that, when the barrel member is moved proximally over the clip arms, the clip arms are constrained toward the closed configuration, and when the barrel member is slid distally along the clip arms, the clip arms are permitted to revert to their biased open configuration.

12. A reverse anastomosis clipping system, comprising:
a lumen-apposing metal stent configured to provide a temporary pathway between a first structure along a gastrointestinal tract and a second structure further along the gastrointestinal tract than the first structure via a first tissue perforation through a wall of the first structure and a second tissue perforation through a wall of the second structure;
a clip configured to be inserted into the second structure via the second tissue perforation upon removal of the lumen-apposing metal stent to close the second tissue perforation from an interior of the second structure, the clip including a pair of clip arms, distal ends of which are connected to one another and received within a cavity of a barrel member to be moved relative thereto between an open configuration, in which proximal ends of the clip arms are separated from one another, and a closed configuration, in which the proximal ends of the clip arms are moved toward one another;
a longitudinal member extending from a proximal end to a distal end and including a lumen extending therethrough, the longitudinal member positioned between the clip arms such that the distal end of the longitudinal member is pressed distally against the distal ends of the clip arm to hold the clip arms distally against the barrel member; and
a control member slidably received within the lumen of the longitudinal member, the control member extending from a proximal end to a distal end that extends distally past the distal end of the longitudinal member and the distal ends of the clip arms to be releasably connected to the distal end of the barrel member, a longitudinal movement of the control member relative to the longitudinal member moving the clip arms between the open and closed configurations.

13. The system of claim 12, wherein the distal end of the control member is an enlarged ball received within a correspondingly shaped socket along a proximal face of a distal end of the barrel member, the enlarged ball connected to a remaining length of the control member via a joint configured to separate the enlarged distal end from the remaining length when subject to a force exceeding a predetermined threshold value.

14. The system of claim 12, wherein the proximal end of each of the clip arms includes a pair of fingers, each of the fingers extending along opposing sides of the longitudinal member when the clip is in the closed configuration so that each of the fingers of a first one of clip arms extends toward a corresponding finger of a second one of the clip arms.

15. The system of claim 12, wherein each of the clip arms including a locking tab extending laterally outward therefrom and configured to engage a corresponding window extending through a wall of the barrel member to lock the barrel member over the clip arms in the closed configuration.

* * * * *